United States Patent [19]
Olesen

[11] Patent Number: 5,936,088
[45] Date of Patent: Aug. 10, 1999

[54] SUBSTITUTED AZACYCLIC OR AZABICYCLIC COMPOUNDS WITH AFFINITY AND SELECTIVITY FOR NICOTINIC CHOLINERGIC RECEPTORS

[75] Inventor: Preben Houlberg Olesen, Copenhagen, Denmark

[73] Assignee: Novo Nordisk A/S, Bagsvaerd, Denmark

[21] Appl. No.: 09/043,628

[22] PCT Filed: Sep. 20, 1996

[86] PCT No.: PCT/DK96/00402

§ 371 Date: Mar. 20, 1998

§ 102(e) Date: Mar. 20, 1998

[87] PCT Pub. No.: WO97/11073

PCT Pub. Date: Mar. 27, 1997

[30] Foreign Application Priority Data

Sep. 22, 1995 [DK] Denmark ................... 1064/95

[51] Int. Cl.[6] ............ C07D 453/02; C07D 471/08; C07D 205/06; A61K 31/445; A61K 31/40
[52] U.S. Cl. ............ 546/133; 514/183; 514/214; 514/249; 514/299; 514/305; 514/413; 540/523; 546/112; 548/515

[58] Field of Search ............... 546/133, 112; 548/515; 540/523; 514/305, 413, 249, 299, 183, 214

[56] References Cited

U.S. PATENT DOCUMENTS

| | | | |
|---|---|---|---|
| 3,857,848 | 12/1974 | Mauvernay et al. | 546/133 |
| 3,899,498 | 8/1975 | Grethe et al. | 546/133 |
| 4,937,239 | 6/1990 | Lauffer et al. | 514/183 |
| 5,110,828 | 5/1992 | Bromidge et al. | 514/413 |
| 5,166,357 | 11/1992 | Orlek et al. | 514/299 |
| 5,183,893 | 2/1993 | Galliani et al. | 546/133 |

FOREIGN PATENT DOCUMENTS

| | | | |
|---|---|---|---|
| 0 414 394 | 2/1991 | European Pat. Off. | |
| 0 638 569 | 2/1995 | European Pat. Off. | |
| 94/20496 | 9/1994 | WIPO | 546/133 |

*Primary Examiner*—Floyd D. Higel
*Attorney, Agent, or Firm*—Steve T. Zelson; Carol E. Rozek

[57] ABSTRACT

The present invention relates to therapeutically active azacyclic and azabicyclic compounds, to methods for their preparation and to pharmaceutical compositions comprising the compounds. These compounds are useful in treating diseases in the central nervous system related to malfunctioning of the nicotinic cholinergic system.

13 Claims, No Drawings

SUBSTITUTED AZACYCLIC OR AZABICYCLIC COMPOUNDS WITH AFFINITY AND SELECTIVITY FOR NICOTINIC CHOLINERGIC RECEPTORS

CROSS-REFERENCE TO RELATED APPLICATIONS

This application is a 35 U.S.C. 371 national application of PCT/DK96/00402 filed Sep. 20, 1996 and claims priority under 35 U.S.C. 119 of Danish application 1064/95 filed Sep. 22, 1995, the contents of which are fully incorporated herein by reference.

FIELD OF THE INVENTION

The present invention relates to heterocyclic compounds which are cholinergic ligands selective for neuronal nicotinic channel receptors, to methods for their preparation, to pharmaceutical compositions comprising them, and to their use in treating cognitive, neurological and mental disorders, such as dementia and anxiety, which are characterized by decreased cholinergic function. The invention also relates to a method of treating Parkinson's disease by modulating the process of dopamine secretion, a method of treating or preventing withdrawal symptoms caused by cessation of chronic or long term use of tobacco products, as well as a method for treating obesity.

BACKGROUND OF THE INVENTION

Nicotinic and muscarinic receptors are the two distinct types of cholinergic receptors named after their selectivity for muscarine and nicotine, respectively. The cholinergic system is the neurotransmitter system that best correlates with memory and cognitive functions. Traditionally, the cholinergic hypothesis for senile dementia of the Alzheimer type (SDAT) has focused on muscarinic acetylcholine receptors (mAChR), and only recently an interest in the role of the nicotinic acetylcholine receptors (nAChR) in SDAT has emerged. This interest was spurred by the relatively recent discovery that nAChR are not only located on the skeletal muscle but also in the brain.

It has been shown that the number of nAChR were decreased in SDAT patients (Nordberg et al. J. Neurosci. Res. Vol. 31, pp. 103–111 (1992); Giacobini Advances in Experimental Medicine and Biology, Vol. 296, pp. 9205–9295, (1993); Schroeder et al., Neurobiol. of Aging, Vol. 12, pp. 259–262, (1991); Whitehouse et al., Neurology, Vol. 38, pp. 720–723, (1988); Flynn and Mash, J. Neurochem., Vol. 47, pp. 8702–8702, (1993)). Similar deficiencies in choline acetyltransferase activity and acetylcholine synthesis suggest that presynaptic receptors on cholinergic nerve terminals are preferentially lost in SDAT (Nordberg, J. Reprod. Fert. Suppl., Vol 46, pp. 145–154, (1993)). Therefore, it has been assumed that the loss of nAChR may correlate with age related onset of disorders of memory and cognitive functions, and that nicotinic replacement therapy may prove beneficial in SDAT. Indeed nicotine improved attention and memory in healthy humans (Warburton, Prog. Neuro. Psychopharmacol. Biol. Psychiatry, Vol. 16, pp. 181–191, (1992)) as well as in Alzheimer's disease patients, (Jones et al. Psychopharmacology, Vol. 108, pp. 485–494, (1992); Gitelman and Prohovnik, Neurobiol. of Aging, Vol. 13, pp. 313–318, (1992); Newhouse et al., Psychopharmacology, Vol. 95, pp. 171–175, (1988); Sahakian et al., Br. J. Psychiatry, Vol. 154, pp. 9004–904, (1993)). Further the nicotinic antagonist mecamylamine has been shown to cause cognitive impairment in an age related way,—(Newhouse et al., Neuropsychopharmacology, Vol 10, pp. 93–107, (1994)).

Parkinson's disease (PD) is a debilitating neurodegenerative disease, presently of unknown etiology, characterized by tremors and muscular rigidity. There is evidence that nicotine may also have beneficial effects in PD. Studies show that smoking may protect against the development of PD, (Ishikawa and Mmiyatake, J. Neurol. Sci., Vol. 117, pp. 28–32, (1993); Godwin-Austen et al., J. Neurol. Neurosurg. Psychiat., Vol. 45, pp. 577–581, (1982); Reavill, in Nicotine psychopharmacology: Molecular, cellular and behavioral aspects, pp. 307–340, Oxford University Press, (1990)), and that chronic nicotine may protect against cell loss in the substantia nigra caused by lesioning (Janson and Moller, Neuroscience, Vol. 57, 931–941, (1993)). Nicotine has also shown beneficial effects in Tourette's syndrome (Sanberg et al., Biomed. Phamacother., Vol. 43, pp. 19–23, (1989)). Alleviation of negative psychotic symptoms, known as the hypofrontality syndrome in schizophrenia, by nicotinic agonists, have been suggested by data showing that nicotine stimulates dopamine release in the nucleus accumbens more potently than in striatum, (Rowell et al. J. Neurochem., Vol. 49, pp. 1449–1454, (1987); Giorguieff-Chesselet et al., Life Sciences, Vol. 25, pp. 1257–1262, (1979)), by nicotinic reversal of inactivation of prefrontal neurons (Svenson et al., In the Biology of Nicotine dependence., pp. 169–185, New York, (1990)), and by the observation that nicotine will potentiate dopaminergic effects in various behavioral models, (Reavill, in Nicotine psychopharmacology: Molecular, cellular and behavioral aspects, pp. 307–340, Oxford University Press, (1990); Rosecrans et al., Psychopharmacol. Commmun., Vol. 2, pp. 349–356, (1976); Reavill and Stolerman, J. Psychopharmacol., Vol. 1, pp. 264, (1987)).

In recent years there have been several studies on the effects of nicotine and food consumption and associated changes in body weight in rat and human. (Greenberg et al., Addictive behaviours, Vol. 7, pp. 317–331, (1982) and Greenberg et al., Psychopharmacology, Vol. 90, pp. 101–105, (1984)). The appetite effects of nicotine have been suggested to be mediated via modulation of CCK peptides in the paraventricular hypothalamic nucleus (Fuxe et al., Acta Physiologica Scandinavica, Vol. 125, pp. 437–443, (1985)).

DESCRIPTION OF THE INVENTION

It is an object of the invention to provide novel heterocyclic compounds with affinity and selectivity for nicotinic cholinergic receptors, to methods for their preparation, to pharmaceutical compositions containing them, and to their use in treating Alzheimer's disease, Parkinson's disease, Tourette's syndrome, ulcerative colitis, obesity, other central nervous system and gastrointestinal disorders as well as severe pain.

The present invention relates to novel substituted azacyclic or azabicyclic compounds of formula Ia, Ib and Ic selected from the following:

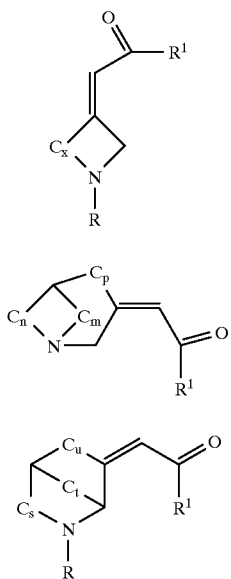

wherein
x is 1, 2, 3, 4 or 5; and
n is 1, 2 or 3; and
m is 1, 2 or 3; and
p is 0, 1 or 2; and
s is 0, 1 or 2; and
t is 0, 1 or 2; and
u is 0, 1 or 2; and
R is hydrogen or $C_{1-6}$-alkyl; and
$R^1$ is hydrogen, $C_{1-6}$-alkyl, $C_{2-6}$-alkenyl, $C_{2-6}$-alkynyl, $C_{3-6}$-cycloalkyl, $C_{1-6}$-polyfluoroalkyl, $C_{2-6}$-alkoxyalkyl, $C_{2-6}$-alkylthioalkyl or $C_{2-6}$-alkylaminoalkyl, or a pharmaceutically acceptable salt thereof.

Examples of such salts include inorganic and organic acid addition salts such as hydrochloride, hydrobromide, sulphate, phosphate, acetate, fumarate, maleate, citrate, lactate, tartrate, oxalate, or similar pharmaceutically-acceptable inorganic or organic acid addition salts, and include the pharmaceutically acceptable salts listed in Journal of Pharmaceutical Science, 66, 2 (1977) which are hereby incorporated by reference.

The compounds of formula Ia, Ib or Ic may exist as geometric and optical isomers and all isomers and mixtures thereof are included herein. Isomers may be separated by means of standard methods such as chromatographic techniques or fractional crystallization of suitable salts.

The term "$C_{1-3}$-alkyl" and "$C_{1-6}$-alkyl" as used herein, alone or in combination, refers to a straight or branched, saturated hydrocarbon chain having the indicated number of carbons such as for "$C_{1-3}$-alkyl" methyl, ethyl, n-propyl and isopropyl and for "$C_{1-6}$-alkyl" methyl, ethyl, n-propyl, isopropyl, n-butyl, sec. butyl, isobutyl, tert. butyl, n-pentyl, 2-methylbutyl, 3-methylbutyl, n-hexyl, 4-methylpentyl, neopentyl, n-hexyl and 2,2-dimethylpropyl and the like.

The term "$C_{3-6}$-cycloalkyl" as used herein refers to a radical of a saturated cyclic hydrocarbon having from 3 to 6 carbon atoms such as cyclopropyl, cyclobutyl, cyclopentyl or cyclohexyl and the like.

The term "$C_{2-6}$-alkenyl" as used herein refers to an unsaturated hydrocarbon chain having from 2 to 6 carbon atoms and at least one double bond such as vinyl, 1-propenyl, allyl, isopropenyl, n-butenyl, n-pentenyl and n-hexenyl and the like.

"Polyfluoro" in "$C_{1-6}$-polyfluoroalkyl" means a $C_{1-6}$-alkyl substituted with from 2 to 13 fluorine atoms such as $-CF_3$, $-CH_2-CF_3$, $-CH_2-CH_2-CF_3$ and $-CH_2-CH_2-CH_2-CF_3$ and the like.

The term "$C_{2-6}$-alkynyl" as used herein refers to an unsaturated hydrocarbon chain having from 2 to 6 carbon atoms and at least one triple bond such as $-C\equiv CH$, $-C\equiv CCH_3$, $-CH_2C\equiv CH$, $-CH_2-CH_2-C\equiv CH$, $-CH(CH_3)C\equiv CH$ and the like.

"$C_{2-6}$-alkoxyalkyl" as used herein means a group of 2 to 6 carbons interrupted by an O such as $-CH_2-O-CH_3$, $-CH_2-CH_2-O-CH_3$ and $-CH_2-O-CH_2-CH_3$ and the like.

"$C_{2-6}$alkylthioalkyl" means a group of 2 to 6 carbons interrupted by an S such as $-CH_2-S-CH_3$, $-CH_2-CH_2-S-CH_3$ and $-CH_2S-CH_2-CH_3$ and the like.

"$C_{2-6}$-alkylaminoalkyl" means a group of 2 to 6 carbons interrupted by an N such as $-CH_2-NH-CH_3$, $-CH_2-CH_2NH-CH_3$, and $CH_2-NH-CH_2-CH_3$ and the like.

In a preferred embodiment of the invention R represents H or $C_{1-3}$-alkyl. For x, a preferred value is 2, 3 or 4, n, m and p is preferably respectively 2, 1 and 0 or 2, 2 and 0 or 3, 1 and 0 and s, t and u is preferably respectively 1, 1 and 0 or 1, 2 and 0 or 1, 2 and 1.

Preferred compounds include:
(Z)-3-acetylmethylene-1-azabicyclo[2.2.2]octane;
(E)-3-acetylmethylene-1-azabicyclo[2.2.2]octane;
(Z)-3-acetylmethylene-1-azabicyclo[2.2.1]heptane;
(E)-3-acetylmethylene-1-azabicyclo[2.2.1]heptane;
(Z)-3-Propionylmethylene-1-azabicyclo(2.2.1)heptane;
(E)-3-Propionylmethylene-1-azabicyclo(2.2.1)heptane;
(Z)-3-Propionylmethylene-1-azacyclo(2.2.2)octane;
(E)-3-Propionylmethylene-1-azacyclo(2.2.2)octane;
or a pharmaceutically acceptable salt thereof.

The invention also relates to a method of preparing the above mentioned compounds of formula Ia, Ib or Ic. These methods comprise:

a) reacting a compound of formula IIa, IIb or IIc selected from the following:

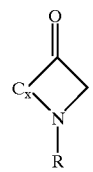

(IIa)

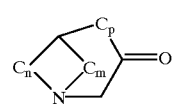

(IIb)

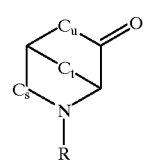

(IIc)

wherein R, x, n, m, p, s, t and U have the meanings defined above with a phosphorus ylide of formula III or a phosphonate of formula IV

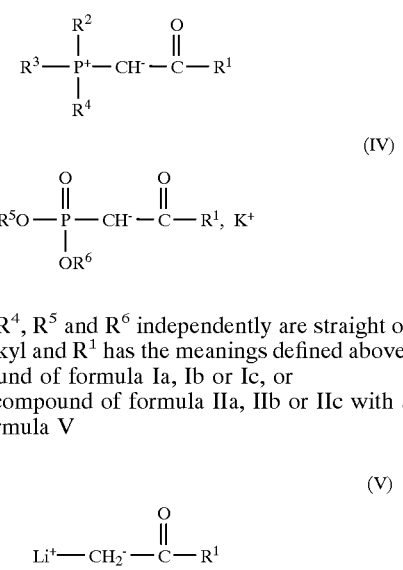

wherein $R^2$, $R^3$, $R^4$, $R^5$ and $R^6$ independently are straight or branched $C_{1-6}$-alkyl and $R^1$ has the meanings defined above, to give a compound of formula Ia, Ib or Ic, or b) reacting a compound of formula IIa, IIb or IIc with a compound of formula V wherein $R^1$ has the meaning defined above followed by dehydration, to give a compound of formula Ia, Ib or Ic.

The pharmacological properties of the compounds of the invention can be illustrated by determining their capability to inhibit the specific binding of $^3$H-methylcarbamylcholine ($^3$H-MCC) (Abood and Grassi, Biochem. Pharmacol., Vol. 35, pp. 4199–4202, (1986)).

$^3$H-MCC labels the nicotinic receptors in the CNS. The inhibitory effect on $^3$H-MCC binding reflects the affinity for nicotinic acetylcholine receptors.

Fresh or frozen rat, brain tissue (hippocampus or cortex) was homogenized in assay buffer (50 mM Tris-HCl, pH 7.4, 120 mM NaCl, 5 mM KCl, 2 mM $CaCl_2$, 1 mM $MgCl_2$) and centrifuged for 10 min. at 40.000×g. Pellets were subsequently reconstituted in assay buffer and an appropriate amount of tissue sample was mixed in tubes with $^3$H-methylcarbamylcholine (NEN, NET-951; final concentration 2 nM) and test drug. The tubes were incubated at 0° C. for 60 min. Unbound ligand was separated from bound ligand by vacuum filtration through GF/B filters presoaked in 0.5% polyethylenimine. Filters were washed three times with 5 ml wash buffer (50 mM Tris-HCl, pH 7.4) and transferred to vials. 4 ml scintillation fluid was added and the radioactivity was measured by scintillation counting. Unspecific binding was measured with 10 $\mu$M nicotine.

The $IC_{50}$ values of the test compounds were determined by nonlinear regression analyses (GraphPad InPlot).

Furthermore, the pharmacological properties of the compounds of the invention can also be illustrated by determining their capability to inhibit the specific binding of $^3$H-Oxotremorine-M ($^3$H-Oxo). Birdsdall N. J. M., Hulme E. C., and Burgen A. S. V. (1980). "The Character of Muscarinic Receptors in Different Regions of the Rat Brain". Proc. Roy. Soc. London (Series B) 207,1.

$^3$H-Oxo labels muscarinic receptor in the CNS (with a preference for agonist domains of the receptors). Three different sites are labelled by $^3$H-Oxo. These sites have affinity of 1.8, 20 and 3000 nM, respectively. Using the present experimental conditions only the high and medium affinity sites are determined.

The inhibitory effects of compounds on $^3$H-Oxo binding reflects the affinity for muscarinic acetylcholine receptors.

All preparations are performed at 0–4° C. unless otherwise indicated. Fresh cortex (0.1–1 g) from male Wistar rats (150–250 g) is homogenized for 5–10 s in 10 ml 20 mM Hepes pH: 7.4, with an Ultra-Turrax homogenizer. The homogenizer is rinsed with 10 ml of buffer and the combined suspension centrifuged for 15 min. at 40,000×g. The pellet is washed three times with buffer. In each step the pellet is homogenized as before in 2×10 ml of buffer and centrifuged for 10 min. at 40,000×g.

The final pellet is homogenized in 20 mM Hepes pH: 7.4 (100 ml per g of original tissue) and used for binding assay. Aliquots of 0.5 ml is added 25 ul of test solution and 25 ul of $^3$H-Oxotremorine (1.0 nM, final concentration) mixed and incubated for 30 min. at 25° C. Non-specific binding is determined in triplicate using arecoline (1 ug/ml, final concentration) as the test substance. After incubation samples are added 5 ml of ice-cold buffer and poured directly onto Whatman GF/C glass fiber filters under suction and immediately washed 2 times with 5 ml of ice-cold buffer. The amount of radioactivity on the filters are determined by conventional liquid scintillation counting. Specific binding is total binding minus non specific binding.

Test substances are dissolved in 10 ml water (if necessary heated on a steam-bath for less than 5 min.) at a concentration of 2.2 mg/ml. 25–75% inhibition of specific binding must be obtained before calculation of $IC_{50}$. The test value will be given as $IC_{50}$ (the concentration (nM) of the test substance which inhibits the specific binding of $^3$H-Oxo by 50%).

$$IC_{50} = \text{(applied test substance concentration)} \times (C_x/C_o-C_x)\text{nM}$$

where $C_o$ is specific binding in control assays and $C_x$ is the specific binding in the test assay. (The calculations assume normal mass-action kinetics).

Table I illustrates the affinity of the compounds of the present invention for nicotinic and muscarinic receptors as determined by $^3$H-MCC and $^3$H-Oxo binding to rat cortical receptors. The compounds, however, show selective affinity for nicotinic receptors as compared to muscarinic receptors, i.e OXO/MCC>1.

TABLE 1

| Compound | $^3$H-MCC $IC_{50}$ nM | $^3$H-Oxo $IC_{50}$ nM | Oxo/MCC Ratio |
|---|---|---|---|
| 1 | 23 | 1200 | 52 |
| 2 | >300 | <1000 | |

The compounds of the invention are effective over a wide dosage range. For example, in the treatment of adult humans, dosages from about 0.05 to about 100 mg, preferably from about 0.1 to about 100 mg, per day may be used. A most preferable dosage is about 10 mg to about 70 mg per day. In choosing a regimen for patients suffering from diseases in the central nervous system caused by malfunctioning of the nicotinic cholinergic system it may frequently be necessary to begin with a dosage of from about 30 to about 70 mg per day and when the condition is under control to reduce the dosage as low as from about 1 to about 10 mg per day. The exact dosage will depend upon the mode of administration, form in which administered, the subject to be treated and the body weight of the subject to be treated, and the preference and experience of the physician or veterinarian in charge.

The route of administration may be any route, which effectively transports the active compound to the appropriate or desired site of action, such as oral or parenteral e.g. rectal, transdermal, subcutaneous, intravenous, intraurethral, intramuscular, topical, intranasal, ophthalmic solution or an ointment, the oral route being preferred.

Typical compositions include a compound of formula Ia, Ib or Ic or a pharmaceutically acceptable acid addition salt thereof, associated with a pharmaceutically acceptable carrier. In making the compositions, conventional techniques for the preparation of pharmaceutical compositions may be used. For example, the active compound will usually be mixed with a carrier, or diluted by a carrier, or enclosed within a carrier which may be in the form of a ampoule, capsule, sachet, paper, or other container. When the carrier serves as a diluent, it may be solid, semi-solid, or liquid material which acts as a vehicle, excipient, or medium for the active compound. The active compound can be adsorbed on a granular solid container for example in a sachet. Some examples of suitable carriers are water, salt solutions, alcohols, polyethylene glycols, polyhydroxyethoxylated castor oil, gelatine, lactose, amylose, magnesium stearate, talc, silicic acid, fatty acid monoglycerides and diglycerides, pentaerythritol fatty acid esters, hydroxymethylcellulose and polyvinylpyrrolidone.

The pharmaceutical preparations can be sterilized and mixed, if desired, with auxiliary agents, emulsifiers, salt for influencing osmotic pressure, buffers and/or colouring substances and the like, which do not deleteriously react with the active compounds.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

Generally, the compounds are dispensed in unit form comprising from about 1 to about 100 mg in a pharmaceutically acceptable carrier per unit dosage.

A typical tablet, appropriate for use in this method, may be prepared by conventional tabletting techniques and contains:

| | |
|---|---|
| Active compound | 5.0 mg |
| Lactosum | 67.8 mg Ph.Eur. |
| Avicel ® | 31.4 mg |
| Amberlite ® | 1.0 mg |
| Magnesii stearas | 0.25 mg Ph.Eur. |

The invention will now be described in further detail with reference to the following examples:

EXAMPLE 1

(Z)-3-Acetylmethylene-1-azabicyclo[2.2.2]octane oxalate

To a solution of 3-quinuclidinone (2.0 g, 16 mmol) and potassiumhydroxide (1.93 g, 30 mmol) in water cooled to −5° C. (7.7 ml), dimethyl 2-oxopropylphosphonate (4.9 g, 30 mmol) was added dropwise. The reaction mixture was stirred at a temperature between 0° C. to −5° C. for 90 hours. The reaction mixture was quenched with 1 M hydrochloric acid solution (50 ml), rinsed three times with ether, made basic with solid potassiumcarbonate and extracted with methylenchloride (5×50 ml). The solvent was removed after drying over magnesiumsulfate. The crude compound was crystallised as the oxalate salt from ethanol (100 ml) and then recrystallised from ethanol (50 ml) to give the title compound in 21% yield. M.p. 189–190° C. (Compound 1).

(E)-3-Acetylmethylene-1-azabicyclo[2.2.2]octane oxalate

The mother liquors from the crystallisation of (Z)-3-Acetylmethylene-1-azabicyclo[2.2.2]octane oxalate (Compound 1), was evaporated and titurated with acetone, giving the title compound in 13% yield of 80% purity. M.p. 178–179° C.(Compound 2)

In exactly the same manner the following compounds were prepared:

(Z)-3-Acetylmethylene-1-azabicyclo[2.2.1]heptane oxalate from 1-azabicyclo[2.2.1]heptan-3-one and dimethyl 2-oxopropylphosphonate. M.p. 176–177° C. (Compound 3).

(E)-3-Acetylmethylene-1-azabicyclo[2.2.1]heptane oxalate from 1-azabicyclo[2.2.1]heptan-3-one and dimethyl 2-oxopropylphosphonate. M.p. 168–170° C. (Compound 4.)

(Z)-3-Propionylmethylene-1-azabicyclo(2.2.1)heptane oxalate from 1-azabicyclo(2.2.1)heptan-3-one and dimethyl 2-oxobutylphosphonate. Compound 5. Mp 150–51° C.

(E)-3-Propionylmethylene-1-azabicyclo(2.2.1)heptane oxalate from 1 -azabicyclo(2.2.1)heptan-3-one and dimethyl 2-oxobutylphosphonate. Compound 6. Mp 129–130° C.

(Z)-3-Propionylmethylene-1-azacyclo(2.2.2)octane oxalate from 1-azabicyclo(2.2.2)octan-3-one and dimethyl 2-oxobutylphosphonate. Compound 7. Mp 157–58° C.

(E)-3-Propionylmethylene-1-azacyclo(2.2.2)octane oxalate from 1-azabicyclo(2.2.2)octan-3-one and dimethyl 2-oxobutylphosphonate. Compound 8. Mp 142–43° C.

N-benzhydryl-3-(acetylmethylene)azetidine from N-benzhydrylazitidine-3-one and dimethyl 2-oxopropylphosphonate.

EXAMPLE 2

3-(Acetylmethylene)azetidine hydrochloride

To a solution of N-benzhydryl-3-(acetylmethylene) azetidine (0.35 g, 1.1 mmol) in dichloromethane (10 ml) was added 1-chloroethylchloroformate (0.2 g, 1.3 mmol). The reaction mixture was stirred at room temperature for 20 min. The reaction mixture was evaporated and methanol (30 ml) was added. The reaction mixture was heated at reflux for 40 min, then evaporated. Ether was added and the separated crystal was filtered. Compound 9.

What is claimed is:

1. A compound of formula Ia, Ib or Ic

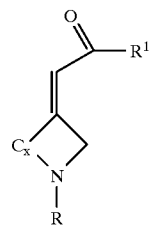

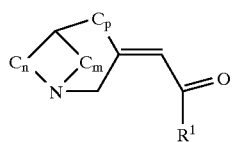
(Ib)

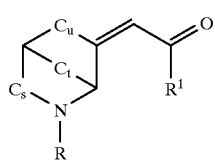
(Ic)

wherein x is 1, 2, 3, 4 or 5; and n is 1, 2 or 3; and m is 1, 2 or 3; and p is 0, 1 or 2; and s is 0, 1 or 2; and t is 0, 1 or 2; and u is 0, 1 or 2; and R is hydrogen or $C_{1-6}$-alkyl; and $R^1$ is hydrogen, $C_{1-6}$-alkyl, $C_{2-6}$-alkenyl, $C_{2-6}$-alkynyl, $C_{3-6}$-cycloalkyl, $C_{1-6}$-polyfluoroalkyl, $C_{2-6}$-alkoxyalkyl, $C_{2-6}$-alkylthioalkyl or $C_{2-6}$-alkylaminoalkyl, or a pharmaceutically acceptable salt thereof.

2. A compound according to claim 1 wherein R is H or $C_{1-3}$-alkyl.

3. A compound according to claim 1 wherein x is 2, 3 or 4.

4. A compound according to claim 1 wherein n, m and p is respectively 2, 1 and 0 or 2, 2 and 0 or 3, 1 and 0.

5. A compound according to claim 1 wherein s, t and u is respectively 1, 1 and 0 or 1, 2 and 0 or 1, 2 and 1.

6. A compound according to claim 1 selected from the following:
(Z)-3-acetylmethylene-1-azabicyclo[2.2.2]octane;
(E)-3-acetylmethylene-1-azabicyclo[2.2.2]octane;
(Z)-3-acetylmethylene-1-azabicyclo[2.2.1]heptane;
(E)-3-acetylmethylene-1-azabicyclo[2.2.1]heptane;
(Z)-3-Propionylmethylene-1-azabicyclo(2.2.1)heptane;
(E)-3-Propionylmethylene-1-azabicyclo(2.2.1)heptane;
(Z)-3-Propionylmethylene-1-azacyclo(2.2.2)octane;
(E)-3-Propionylmethylene-1-azacyclo(2.2.2)octane;
and a pharmaceutically acceptable salt thereof.

7. A method of preparing a compound according to claim 1, comprising a) reacting a compound of formula IIa, IIb or IIc selected from the following:

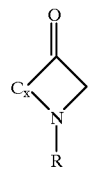
(IIa)

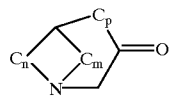
(IIb)

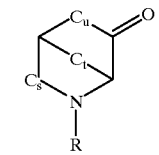
(IIc)

with a phosphorus ylide of formula III or a phosphonate of formula IV

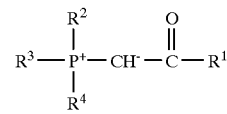
(III)

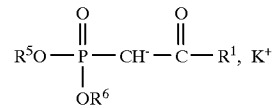
(IV)

wherein $R^2$, $R^3$, $R^4$, $R^5$ and $R^6$ independently are straight or branched $C_{1-6}$-alkyl and to give a compound of formula Ia, Ib or Ic; or b) reacting a compound of formula IIa, IIb or IIc with a compound of formula V

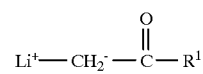
(V)

wherein followed by dehydration, to give a compound of formula Ia, Ib or Ic.

8. A pharmaceutical composition comprising as active component a compound according to claim 1 together with a pharmaceutically acceptable carrier or diluent.

9. A pharmaceutical composition suitable for treating a disease in the central nervous system related to malfunctioning of the muscarinic nicotinic system comprising an effective amount of a compound according to claim 1 together with a pharmaceutically acceptable carrier or diluent.

10. The pharmaceutical composition according to claim 8 in the form of an oral dosage unit or parenteral dosage unit.

11. The pharmaceutical composition according to claim 9, wherein said dosage unit comprises from about 1 to about 100 mg of the compound according to claim 1.

12. A method of treating a central nervous system ailment related to malfunctioning of the nicotinic cholinergic system comprising administering to a subject in need thereof an effective amount of a compound according to claim 1.

13. A method of treating a central nervous system ailment related to malfunctioning of the nicotinic cholinergic system comprising administering to a subject in need thereof a pharmaceutical composition according to claim 8.

* * * * *